United States Patent [19]

Nucci

[11] Patent Number: 5,063,930
[45] Date of Patent: Nov. 12, 1991

[54] DISPOSABLE PROBE FOR THE DETERMINATION OF VAGINAL PH AND OTHER INDICES

[76] Inventor: Prospero Nucci, Via Orio Vergani, 12, 20125 Milan, Italy

[21] Appl. No.: 489,089

[22] Filed: Mar. 6, 1990

[30] Foreign Application Priority Data

Mar. 7, 1989 [IT] Italy ............................ 20688/89[U]

[51] Int. Cl.$^5$ .............................................. A61B 5/00
[52] U.S. Cl. .................... 128/632; 128/636; 128/760; 128/771; 128/778; 606/119
[58] Field of Search ............... 128/632, 636, 738, 760, 128/767, 768, 771, 778; 606/119; 436/163; 116/206

[56] References Cited

U.S. PATENT DOCUMENTS 3,037,496 6/1962 Melges ............................. 128/636
3,117,569 1/1964 Wegner ............................ 128/636
3,701,633 10/1972 Davis ................................ 128/636
4,478,222 10/1984 Koning et al. ................... 128/632
4,632,119 12/1986 Reichstein ........................ 128/632
4,827,944 5/1989 Nugent ............................. 128/771

FOREIGN PATENT DOCUMENTS 8303960 11/1983 PCT Int'l Appl. ................ 128/738

*Primary Examiner*—Lee S. Cohen
*Assistant Examiner*—Krista M. Pfaffle
*Attorney, Agent, or Firm*—Birch, Stewart, Kolasch & Birch

[57] ABSTRACT

A disposable probe made of a transparent plastic material, for the determination of vaginal pH and other indices, including a small pipe with a closed head, a hole provided near the head and one or more pH indicators or other indicators disposed within the probe.

10 Claims, 1 Drawing Sheet

DISPOSABLE PROBE FOR THE DETERMINATION OF VAGINAL PH AND OTHER INDICES

BACKGROUND OF THE INVENTION

The present invention refers to a disposable probe for the determination of the vaginal pH and other indices which presents peculiar characteristics and advantages if compared with the tools commonly used for these purposes.

The vaginal pH is a very important index both of physiological conditions and of pathological states and therefore it should be routinely determined during obstetric-gynecological examinations.

The determination of the vaginal pH allows :
1) A specific diagnosis for various kinds of infections such as for example Candida albicans vaginitis, Trichomonas vaginitis, garderenella vaginitis, mycotic infections, etc.
2) A precocious diagnosis of other pathologies of the genitourinary tract.
3) A determination of the more fertile days.
4) To acquire indications about possible local and systemic alterations.

The vaginal pH, in normal conditions, is comprised between 3.5 and 4.5 but tends to increase when the conditions are alterated because of a patology, local or not, after the administration of medicaments or because of paraphysiological conditions. The use of vaginal pH as a diagnostic tool is however strongly limited by the lack of appropriate instruments for routine determinations.

The commonly used instruments are the vaginal electrical or electronic pH-meters, or the paper pH-indicators. The vaginal pH-meters are a very expensive apparatus while the use of paper pH-indicators by direct contact with the vaginal mucosa is inadvisable since no scientific data showing the absence of a cancerigenic factor of the indicators are at present available.

SUMMARY OF THE INVENTION

We have now found an inexpensive, handy and reliable probe, which allows the routine determination of vaginal pH, overcoming all difficulties and disadvantages of the prior art. Such a probe constists of a small pipe with a closed head and is characterised in that near to said head there is an oval hole while on the internal surface of the head and/or on the internal cylindrical surface, one or more pH-indicators or other indicators are applied.

The characteristics and advantages of the probe according to the present invention will be more evident from the following detailed description, referring to the enclosed explanatory FIGS. 1 and 2.

BRIEF DESCRIPTION OF DRAWINGS

The present invention will become more fully understood from the detailed description given hereinbelow and the accompanying drawings which are given by way of illustration only, and thus, are not limitative of the present invention, and wherein.

DESCRIPTION OF THE PREFERRED EMBODIMENT

Figure 1:
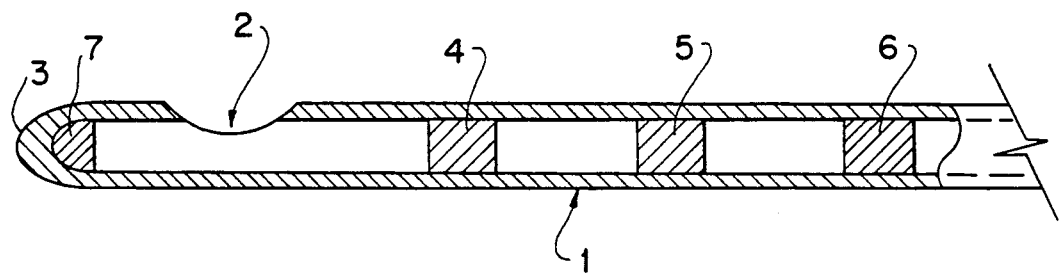
FIG. 1 shows a side view of the probe according to the present invention.
Figure 2:
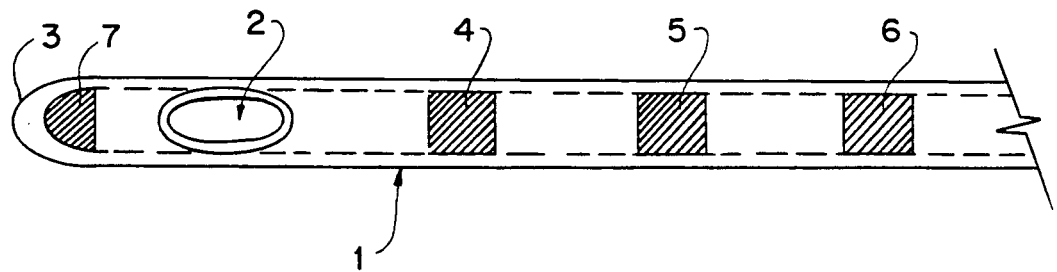
FIG. 2 a plan view of the same probe of Figure 1.

Referring to the reference numerals of FIGS. 1 and 2 the probe, according to the present invention, consists of a small pipe 1 presenting in the wall, near to the head, an oval hole 2 through which the vaginal secretion is collected.

According to the view in the horizontal plane, the rim of such hole is inclined from up to down and from outside to inside, in order to permit an easier collection of the local secretion.

The major diameter of the hole is comprised between 8 and 12 mm. The head 3 of the probe is oval, thoroughly smooth and has an increased thickness with respect of the wall of the pipe 1. On the internal surface of the pipe and on the internal surface of the head are applied one or more indicators, for example in positions 4,5 and 6 opportunely spaced, and in position 7.

One of such indicators can be used for pH determination and particularly for pH values from 3.5 to 8.

In the above positions other indicators can also be utilized (colorimetric, physical, etc.) which can be used for other clinical-diagnostical determinations such as search in situ of Thricomonas vaginalis or manilia, Collins' toluidine blue test, smell test (with KOH), nitrite test.

The probe is made of a transparent plastic material, preferably polyethylene or PVC (medical grade).

The probe is 16–20 cm long and presents an external diameter of 4 –6 mm.; the preferred diameters of the probe are (internal diameter $\times$ external diameter) $2.7 \times 4$ or $3.2 \times 4.7$ or $3.8 \times 5.4$ or $4 \times 6$ mm.

Also other diameters are possible. The plastic material of the probe has a shore value of 94–87.

The indicator is applied inside the pipe with a mechanical injector through automatic operations and in a predetermined dosage. Typically the indicator is applied to the pipe in the form of a liquid solution in a suitable solvent which is then lyophilized so to cause the adhesion of the solid indicator to the internal wall of the pipe.

In other embodiments of the invention, the indicator is firstly absorbed on a non-woven felt or cotton wood or otber absorption solid and small pieces of the thus treated material are introduced in the pipe.

This type of embodiment allows the easy introduction of different indicators into the pipe with the possibility of several chemical-diagnostic determinations by a single test.

For determining the vaginal pH the described probe is introduced in the vagina near to the posterior fornix, the vaginal liquid enters the probe through the hole 2 and flows from the head to the opposite end; the indicator, when it comes into contact with the liquid, reacts giving a color corresponding to the pH of the liquid which can then be compared with a colorimetric scale.

After each measurement the probe is discarded.

The probe according to the present invention presents several advantages compared to the prior art, particularly:

the elimination of the risks connected with a possible local and/or systemic toxicity caused by the contact of the indicator with the vaginal mucosa;
inexpensive to produce;
easiness of use:

possibility of being used with suitable colorimetric or physical indicators according to desired chemical-diagnostic determinations;

elimination of the risk of transmitting bacterical or mycotic infections from one patient to the other including AIDS or hepatitis viruses.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A disposable probe for use in vaginal clinical-diagnostical determinations which comprises an elongated conduit member, said conduit member being made of a transparent plastic material and having at least one closed end portion, an external surface and an internal surface, said internal surface defining an enclosed space, an oval hole, said oval hole being disposed in said conduit member near said closed end portion and extending between said external and internal surfaces for collecting biological fluids, and at least one medial indicator for clinical-diagnostical determinations, each said medical indicator being disposed within said enclosed space.

2. The disposable probe of claim 1 wherein one of said medical indicators is disposed at said closed end portion.

3. The disposable probe of claim 1 wherein, when viewed in the horizontal plate, the oval hole tapers inward from said external surface to said internal surface;

4. The disposable probe of claim 1 wherein each of said medical indicators is applied to said internal surface.

5. The disposable probe of claim 1 wherein one of said medical indicators is a pH indicator for measuring pH values from 3.5 to 8.

6. The disposable probe of claim 1 wherein the major diameter of the hole is between 8 to 12 mm and the external diameter of the probe is from 4 to 6 mm.

7. The disposable probe of claim 1 wherein one of said medical indicators is a pH indicator.

8. The disposable probe of claim 1 wherein one of said medical indicators is a vaginitis indicator.

9. The disposable probe of claim 1 wherein one of said medical indicators is a toluidine blue test indicator.

10. The disposable probe of claim 1 wherein one of said medical indicators is a smell test indicator.

* * * * *